United States Patent
Raugel et al.

(10) Patent No.: US 7,462,180 B2
(45) Date of Patent: Dec. 9, 2008

(54) INSERTER FOR A FLEXIBLE ACETABULAR CUP

(75) Inventors: Patrick Raugel, Ramsey, NJ (US); Loic Pinot, Bernieres sur Mer (FR)

(73) Assignee: Benoist Girard SAS (FR)

( * ) Notice: Subject to any disclaimer, the term of this patent is extended or adjusted under 35 U.S.C. 154(b) by 149 days.

(21) Appl. No.: 11/289,728

(22) Filed: Nov. 29, 2005

(65) Prior Publication Data

US 2006/0167462 A1  Jul. 27, 2006

(30) Foreign Application Priority Data

Dec. 1, 2004  (GB) ................. 0426385.1

(51) Int. Cl.
*A61B 17/58* (2006.01)
*A61B 17/60* (2006.01)

(52) U.S. Cl. .......................................... 606/91; 606/99
(58) Field of Classification Search ................... 606/91, 606/81, 86, 87, 88, 99, 100; 623/22.24, 22.23, 623/22.28, 23.33, 23.35, 23.37, 23.38
See application file for complete search history.

(56) References Cited

U.S. PATENT DOCUMENTS

| | | | |
|---|---|---|---|
| 5,116,339 A | | 5/1992 | Glock |
| 5,571,111 A | * | 11/1996 | Aboczky ...................... 606/91 |
| 5,609,646 A | * | 3/1997 | Field et al. ................ 623/22.32 |
| 5,658,294 A | * | 8/1997 | Sederholm .................... 606/91 |
| 5,904,688 A | * | 5/1999 | Gilbert et al. ................. 606/86 |
| 6,638,311 B2 | * | 10/2003 | Wang et al. ............... 623/22.32 |

FOREIGN PATENT DOCUMENTS

| | | |
|---|---|---|
| DE | 29608453 | 9/1997 |
| GB | 2333961 | 8/1999 |
| WO | 02/074203 | 9/2002 |

* cited by examiner

*Primary Examiner*—Pedro Philogene
(74) *Attorney, Agent, or Firm*—Lerner, David, Littenberg, Krumholz & Mentlik, LLP

(57) ABSTRACT

A prosthesis implantation inserter is used with a flexible acetabular cup which has an opening or openings in its peripheral rim. The inserter has engagement elements which in an operational position frictionally engage the opening or openings in the flexible cup rim. A release is provided which can be operated to withdraw the engagement element from the opening or openings. When the cup is held §in position it can be guided and inserted into the acetabulum and impacted. Once the position of the prosthesis satisfies the surgeon the engagement element can be removed by operating the release and the cup inserter is removed without any risk of compromising the position or the stability of the implant.

20 Claims, 5 Drawing Sheets

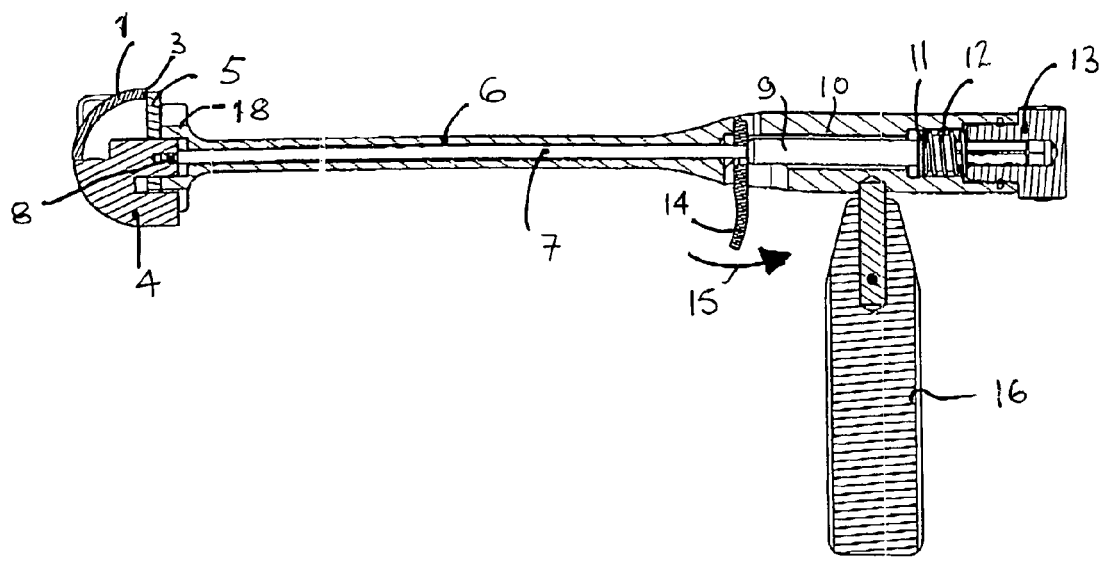
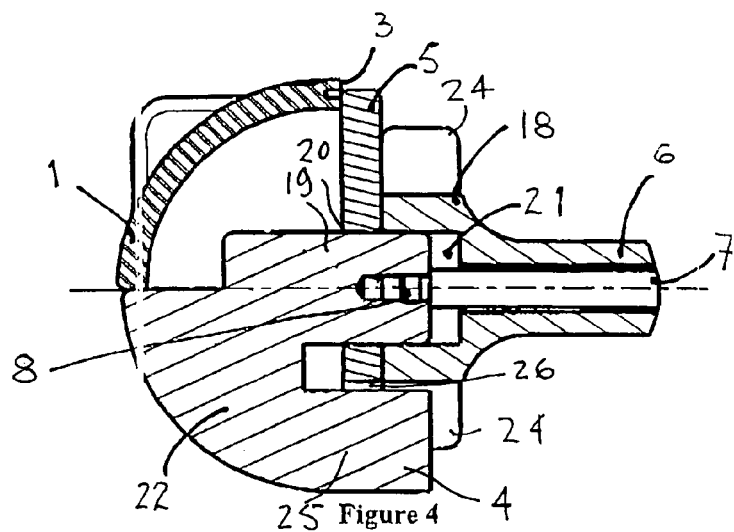
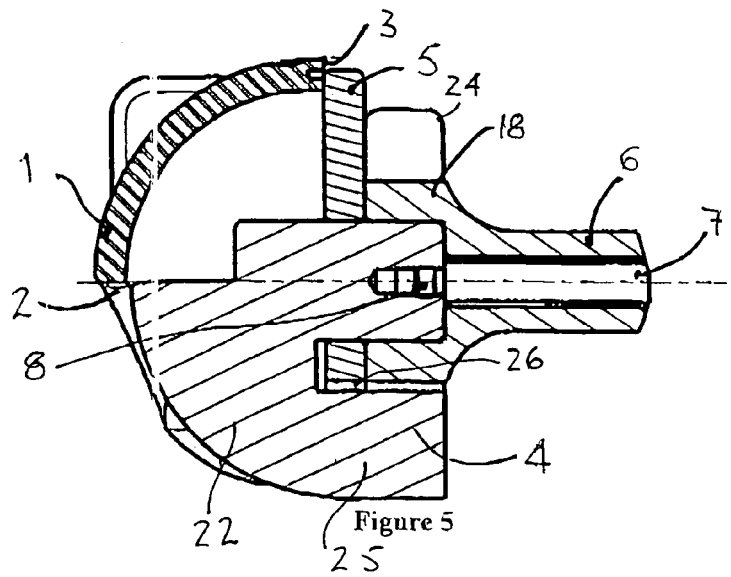
Figure 3
Figure 4
Figure 5

INSERTER FOR A FLEXIBLE ACETABULAR CUP

BACKGROUND OF THE INVENTION

This invention relates to a prosthesis implantation inserter for use with a flexible acetabular cup. Flexible acetabular cups have shown their ability to transfer the load in a natural manner to the patient's pelvis. An acetabular cup of this kind is described in U.S. Pat. No. 5,609,646 the disclosure of which is incorporated herein by reference.

To achieve an initial stability and a long term implantation of a flexible acetabular cup prosthesis it is necessary to ensure that the position of the implant is appropriate and that the contact between the bone and the outer surface of the prosthesis is maximized. Moreover, the stability is achieved due to an interference fit between the host bone cavity and the implant. The outcome during the implantation is its inclination to deform itself. As a consequence, it is difficult to place the acetabular cup adequately and guarantee an intimate contact with the bone. The present invention is intended to provide an instrument to overcome these difficulties.

U.S. Pat. No. 5,954,727 shows a positioning tool for reversibly engaging an acetabular cup, an elongate cylindrical section of the positioning tool being insertable through a posterior opening in the cup. The outer diameter of the cylindrical portion is expandable to engage the inner wall of the cup in an interference fit to prevent movement of the cup relative to the tool and hold the cup in engagement when planting the cup at a desired position.

U.S. Pat. No. 5,098,437 also shows the use of a positioning rod which has spring elements which engage a circumferential groove on the inner surface of the implant.

Neither of these constructions are suitable for use with a flexible acetabular cup due to the flexibility of the cup itself.

In U.S Pat. No. 5,609,646 the flexibility of the cup is provided by the materials from which it is fabricated and a separation or opening in its peripheral rim and the present invention utilizes one opening or separation of this type.

SUMMARY OF THE INVENTION

According to one aspect of the present invention, a prosthesis implantation inserter for use with a flexible acetabular cup which has an opening or openings in its peripheral rim comprises engagement elements which in an operational position frictionally engage the said opening or openings, and a release which can be operated to withdraw the engagement element from the opening or openings.

It will be appreciated that although only one opening is shown in U.S. Pat. No. 5,609,646 a flexible acetabular cup could have a number of openings in its rim and wall to provide the required flexibility. Preferably the engagement element acts to deform the opening or openings when they are engaged thereby in its operational position. The engagement element which contacts the opening or openings can be slightly larger than the opening so that the flexible cup grips the engagement element by friction which acts to secure the cup to the inserter.

When the cup is in position it can be guided and inserted into the acetabulum and impacted. Once the position of the prosthesis satisfies the surgeon the engagement element can be removed by operating the release and the cup inserter is removed without any risk of compromising the position or the stability of the implant.

In a preferred construction the inserter includes a locator adapted to locate the rim of the acetabular cup and in relation to which the engagement element can be moved by the release. Thus the engagement element may comprise a sliding component positioned on the locator.

The engagement element can be resiliently biased towards the operational position and in one preferred embodiment the engagement element can include an engagement portion or portions which is or are shaped to co-operate with the shape of the opening or openings in the peripheral rim of the cup with which it is to be used.

Thus, the engagement portion can be shaped to engage a keyhole-shaped opening in the peripheral rim of the cup with which it is adapted to be used. Alternatively, the engagement portion can be shaped to engage a substantially radially extending slot in the peripheral edge of the cup with which it is to be used.

In another embodiment the engagement portion can be shaped as a series of radially extending fins adapted to engage a series of radially extending openings in the form of slots in the peripheral rim of the cup with which it is to be used.

The locator against which the peripheral rim of the acetabular cup is located can be shaped to accommodate an acetabular cup with a rim which mimics the natural shape of the acetabulum. In a convenient construction the inserter can include a body portion which carries the engagement means, a handle and a trigger which can operate the release means.

Preferably the body portion, handle and trigger are detachable from the engagement element.

The invention also includes a prosthesis implantation inserter in combination with an acetabular cup with which it is to be used.

Also included within the invention is a prosthesis implantation inserter as set forth above in combination with a flexible acetabular cup with which it is to be used and in which the engagement means, detached from the body portion, handle and trigger, and engaged in the cup are located in a sterile package.

BRIEF DESCRIPTION OF THE DRAWINGS

The invention can be performed in various ways and some embodiments will now be described by way of example and with reference to the accompanying drawings in which

FIG. 3 is a cross-sectional side view of the acetabular cup inserter and the acetabular cup shown in FIGS. 1 and 2;

FIG. 4 is an enlarged cross-sectional view of part of the acetabular cup inserter shown in FIG. 3 with the engagement element in its operational position engaged into an opening in the rim of the cup;

FIG. 5 is an enlarged view of part of the cup inserter with the engagement element in its released position;

DETAILED DESCRIPTION

Figure 1:
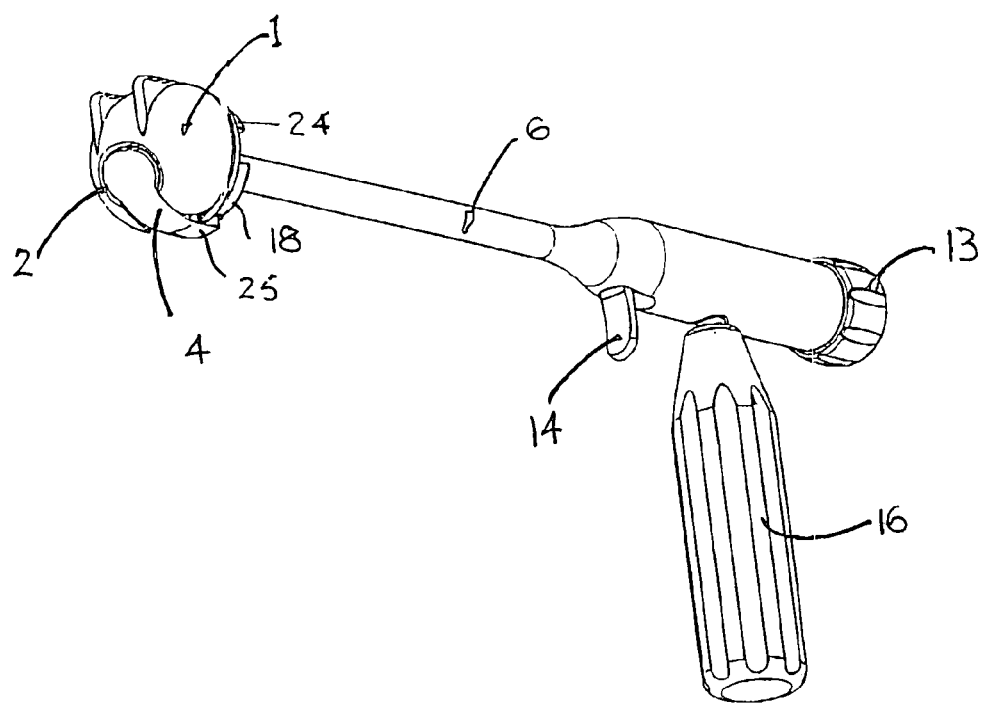
FIG. 1 is an isometric view of an acetabular cup inserter according to the present invention with an acetabular cup in place therein.
Figure 2:
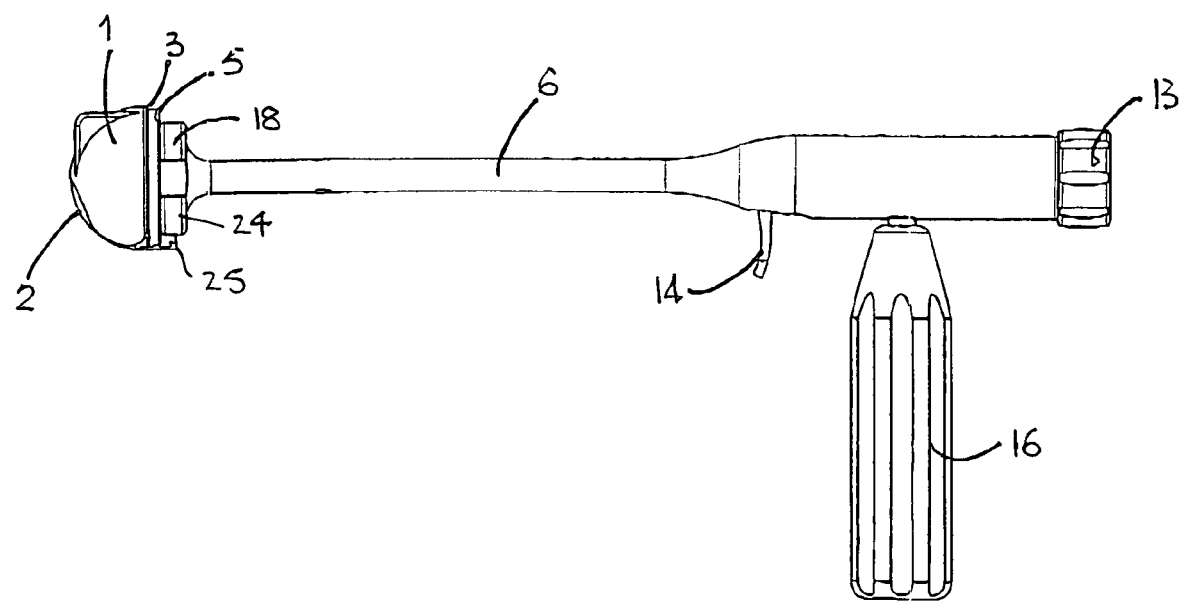
FIG. 2 is a side view of the acetabular cup inserter and an acetabular cup as shown in FIG. 1.
Figure 6:
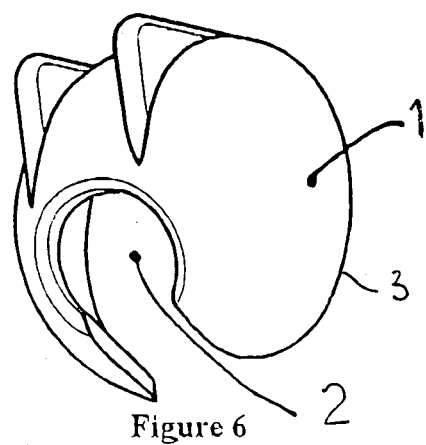
FIG. 6 shows a flexible acetabular cup 1 of the type described in U.S. Pat. No. 5,609,646 and which has a keyhole shaped opening 2 in its peripheral rim 3 for use with the inserter of the present invention.

An inserter, according to the present invention and for use with an acetabular cup 1 as shown in FIG. 6 is shown in FIGS. 1-5 and comprises an engagement element 4 carried on a locator 5 which is mounted on a main body 6 which is in the form of a hollow tube carrying an operating rod 7. One end of the operating rod 7 is screw threaded to locate in and engage a socket 8 in the engagement element 4. The other end of the operating rod 7 is enlarged and indicated by reference numeral 9 and is mounted in an enlarged bore 10. The end of the portion 9 carries a flange 11 which is engaged by a compressed coil spring 12 which is in turn held in place by an end stop 13. The operating rod 7 is therefore biased to the left to force the engagement portion towards the position shown in FIG. 3 and which is its operational position. The engagement element can be withdrawn from its operational position towards the right by a trigger 14 when moved in the direction of the arrow 15.

In the preferred embodiment a handle 16 is provided to facilitate handling.

In FIGS. 4 and 5 the cup 1 to be inserted is shown in position on the inserter. As will most clearly be seen from FIG. 4 the rim 3 of the cup rests against the locator 5 which is in the form of a substantially flat disc and which bears against a flared circumferentially shaped collar 18 on the end of the main body portion 6 which has four arms 24.

Figure 7:
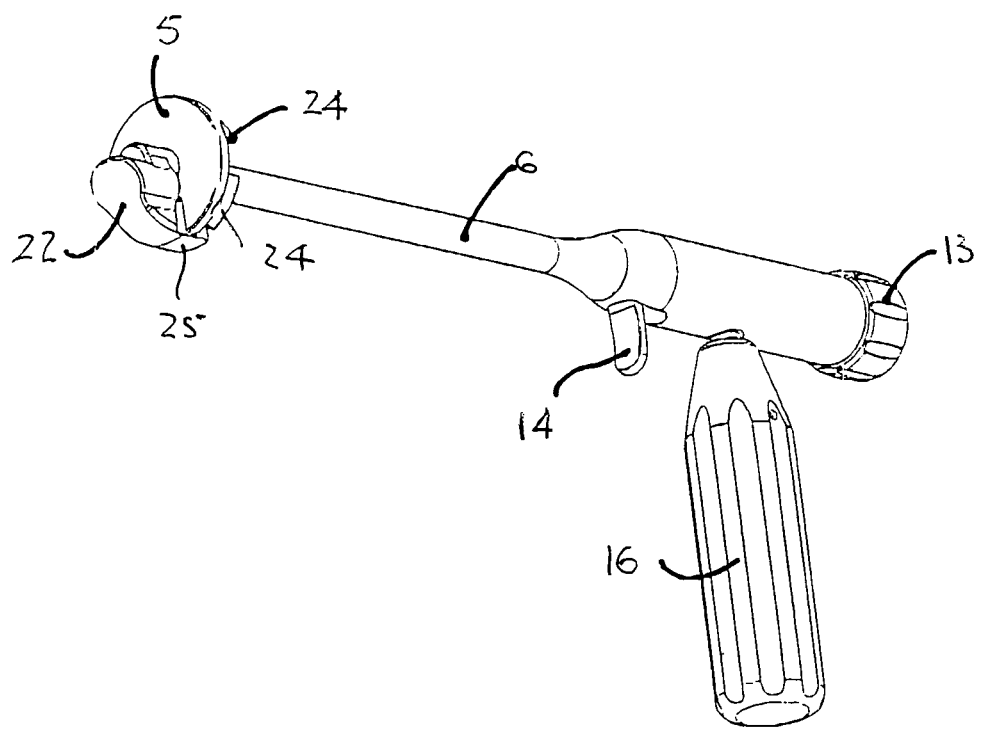
FIG. 7 is an isometric view of the cup inserter without the cup.
Figure 8:
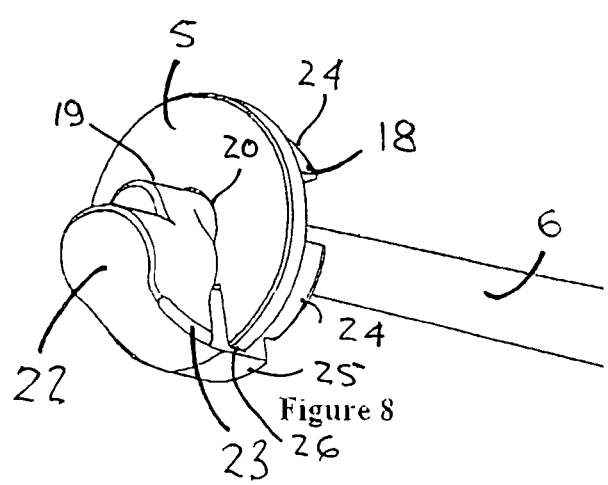
FIG. 8 is an enlarged view of part of the inserter without the cup.
Figure 9:
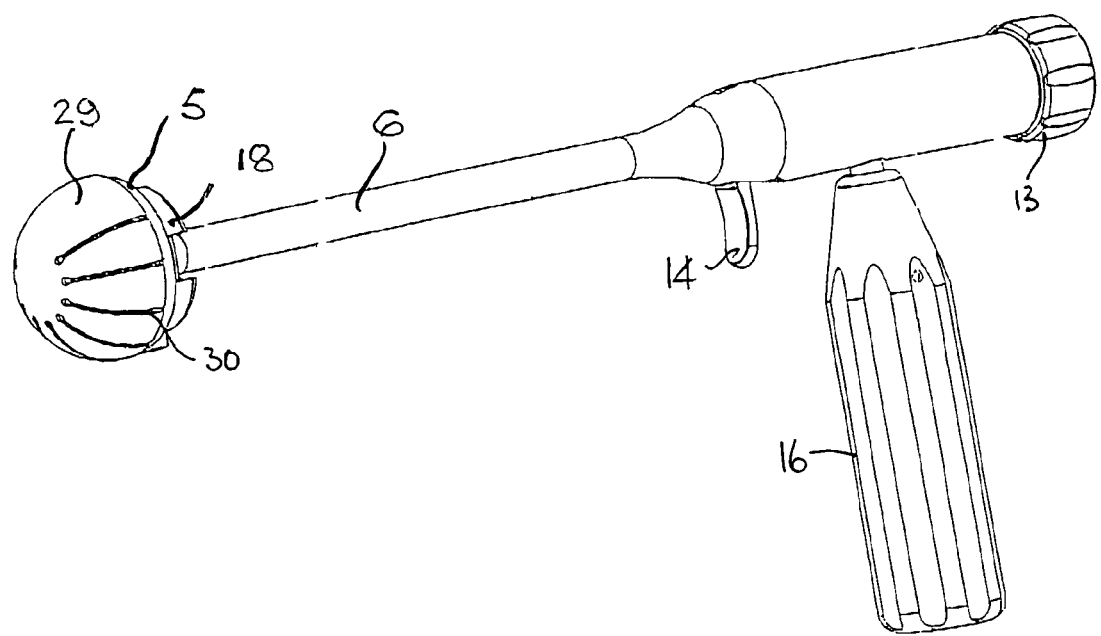
FIG. 9 is an isometric view of an alternative construction of a cup inserter on which a cup with 9 slots is secured.

The overall shape of the engagement element is most clearly shown in FIGS. 7 and 8 and comprises a cylindrical portion 19 which extends through a circular opening 20 in the location plate 5 and extends into a cylindrical socket 21 in the collar 18 as is most clearly shown in FIGS. 4 and 8.

The engagement element 4 also includes a shaped engagement portion 22 whose cross-sectional shape is similar to the cross-sectional shape of the horse shoe shaped opening 2 in the cup to be fitted. The edges of the engagement portion 22 are chamfered, as indicated by reference numeral 23. The dimensions of the engagement portion 22 are slightly larger than the dimensions of the opening 2 with which it is intended to be used. The lower part of the engagement portion 22 also has an extension 25 which acts as a guide between two of the arms 24 and passes through an opening 26 in the location plate 5.

When engagement element 4 is in the operational position, as shown in FIG. 4, the cup to be implanted is pushed over the engagement portion 22 so that, due to its flexible nature, it distorts slightly so that the edges of the opening 2 are gripped by friction on the surface of the engagement portion 22 adjacent its edge. In this position the locator plate 5 is held in position by the shaped collar.

The locator plate 5 can be replaced by smaller or larger plates depending on the outer diameter of the cup 1. Preferably the diameter of the locator plate 5 is smaller than the outer dimensions of the cup 1, as shown in FIGS. 3 and 4, so that the rim 3 of the cup is visible when the cup is secured to the inserter. This is desirable in order to help the surgeon to control the position of the cup in relation with other anatomical landmarks.

The engagement element 4 can be interchangeable with other engagement elements in order to match the specific shape or size of the cup to be implanted.

In order to remove the inserter once the cup has been placed in the acetabulum by the surgeon the trigger 14 is operated in the direction indicated by the arrow 15. This action acts to withdraw the engagement element 4 to the position shown in FIG. 5 thus moving the engagement portion 22 out of the opening 2 and thus releasing the inserter from the cup. The chamfer 23 on the engagement portion 22 assists release.

The position of the "pinch" of the engagement element 4 can be adjusted by changing the shape and the oversize of the engagement portion 22.

Figure 10:
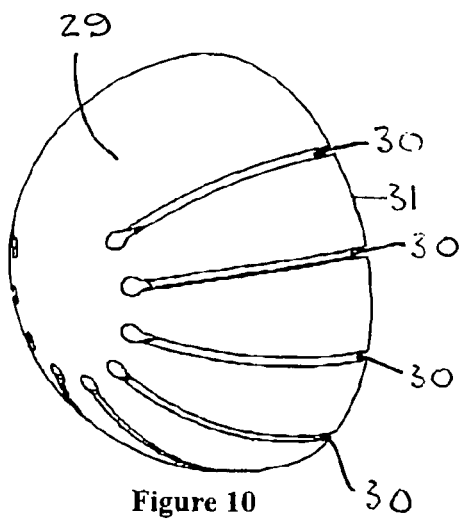
FIG. 10 is an isometric view of a flexible cup of which the flexibility is achieved by 9 slots.
Figure 11:
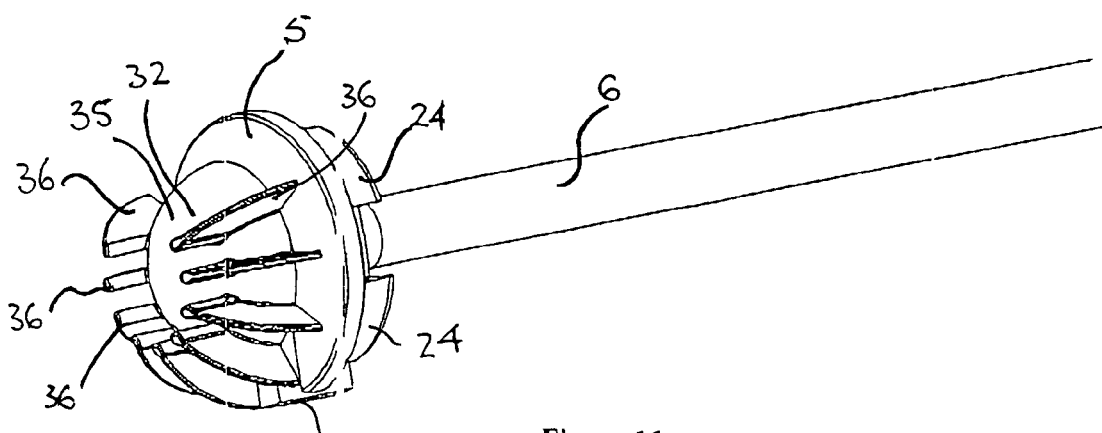
FIG. 11 is an isometric view of part of the cup inserter and the appropriate engagement element for a cup with 9 slots.

The inserter can also be used with flexible cups of alternative constructions, for example the cup 29 shown in FIG. 10. In this construction the flexibility is achieved by replacing the opening 2 of the cup shown in FIG. 6 by a number of slots 30, disposed regularly or not, around the peripheral rim 31 of the cup. In order to operate with this type of cup the engagement element 4 of the construction shown in FIGS. 1 to 8 is replaced by the engagement element 32 shown in FIG. 11. With this arrangement the part of the cylindrical portion 19 which passes through the location plate 5 and enters the socket 21 is retained as is a guide extension 25 which passes between the arms 24, but the outer shaped portion 22 is replaced by a dome 35 and a series of shaped fins 36 which are shaped to engage the slots 30 in the rims 31 of the cup 29. The thickness of the fins is slightly larger than the width of the slots 30 so that there is slight deformation of the cup as it is pushed onto the fins. In the position shown in FIG. 11 the engagement means are in their withdrawn position, that is after the inserter has been removed from the cup. In the operational engagement position the fins will project further outwards and there is allowance at the rear of the fins for the withdrawal action.

Once again the dimensions of the location plate can be adjusted as required with regard to the visible rim 31 of the cup.

The engagement element 32 is held on the operating rod 7 in a similar manner to that described with regard to the earlier construction.

In a further alternative construction (not shown) the number of openings 30 can be reduced in number and the flexibility could even rely on a single slot. To operate with this type of construction the number of fins 36 would be adjusted appropriately.

The material employed to produce the cup 1 or 29 can be composite material such as PEEK, alternatively metal alloys are commonly employed for orthopaedic prostheses such as titanium alloys, cobalt, chromium or molybdenum alloys can be used. They all provide the desired flexibility and the inserter can be used with any of these material cups.

The engagement element 4 and/or the locator plate 5 can be stainless steel alloys commonly employed for producing orthopaedic instruments or other metallic alloys. Alternatively plastics or composite material can be used and in such a case the parts can be made by machining, injection molding or any process suitable with the material concerned.

Figure 12:
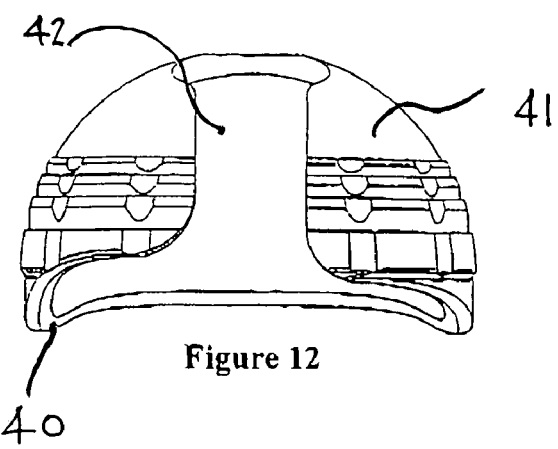
FIG. 12 is a diagrammatic front view of a flexible cup with an anatomic rim.
Figure 13:
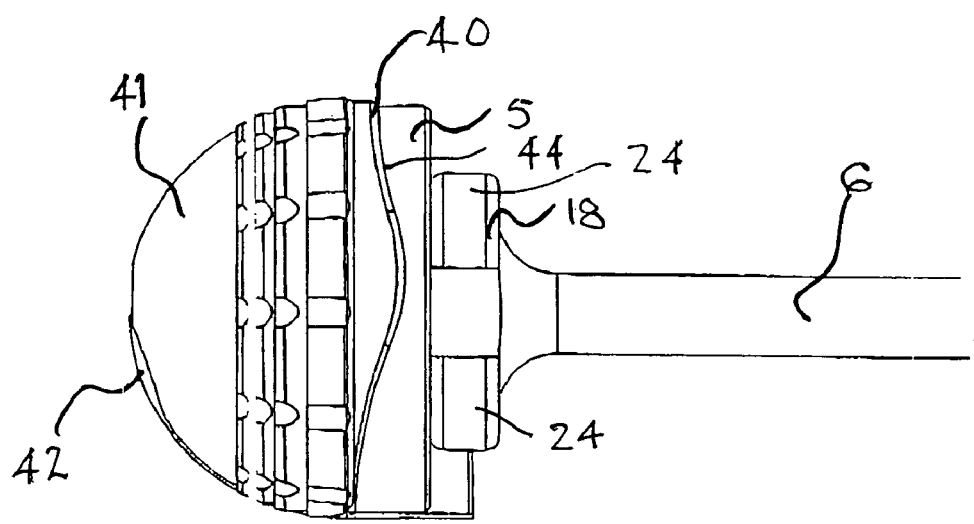
FIG. 13 is a detailed side view of the cup inserter on which is secured a flexible cup with an anatomic rim; and, FIG. 14 is an isometric view of the flexible cup shown in FIG. 12 with the engagement element engaged but removed from the remainder of the inserter.

FIGS. 12 and 13 show how the cup inserter, according to the present invention, can also be used with a cup which has a rim 40 which is shaped with peaks and valleys that mimic the natural shape of the acetabulum, for example of the type shown in U.S. Patent Publication 2005/0060040. The cup 41 shown in FIGS. 12 to 14 has a shaped opening 42 in its rim 40 which is of a keyhole shape similar to the opening 2 in the rim of the cup shown in FIG. 6. In order to accommodate the shaped rim the facing surface 44 of the location plate 5 is shaped appropriately.

Figure 14:
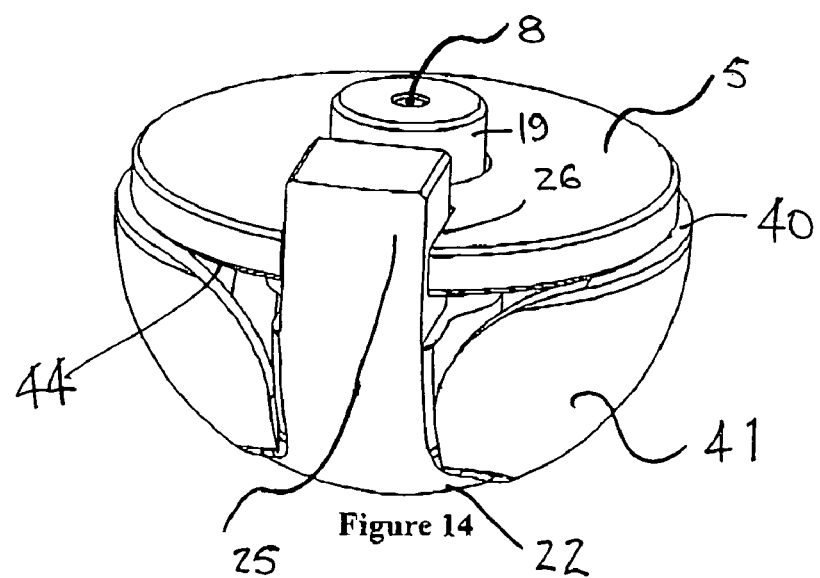

FIG. 14 shows a cup 41 of the kind shown in FIGS. 12 and 13 located on the shaped engagement portion 22 and the engagement means and locator plate 5 removed from the main body portion, trigger and handle. The removal is achieved by unscrewing the operating rod 7 from the socket 8 in the cylindrical portion 19 of the engagement means 4.

The cup 41 which is to be used can be delivered pre-positioned on the engagement means 4 as shown in FIG. 14 in a sterile packaging in order to simplify attaching the cup to the cup inserter. To secure the cup to the inserter, the cylindrical portion 19 is threaded onto the operating rod 7 in the cylindrical socket 21 and tightened by rotating the end stop 13. In such an arrangement the engagement means and/or the location plate 5 can be disposable. Preferably both of these are made of a plastic material and injection molded.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An insertion instrument for a flexible prosthetic acetabular cup, the acetabular cup having a part-spherical outer shell and an inner bearing element with the shell and inner bearing element having at least one opening therein extending from an open end of the shell and bearing element toward a polar area of the shell comprising the opening having a curved periphery:
    a shaft having a mounting element for contacting the open end of the shell at a first end of said shaft;
    a retractable rod element connected to at least one engagement element for resiliently engaging side walls of the opening in the shell and bearing element, the engagement element having curved outer periphery and edges for engaging the curved periphery of the outer shell and bearing element sidewalls, the engagement element having a width greater than a non-expanded width of the opening in a direction parallel to a circumference of the open end and the edges of the engagement element are chamfered; and
    a retractor mounted adjacent a second end of the shaft for moving said engagement element on said rod out of engagement with the sidewalls of the shell while maintaining the mounting element in engagement with the open shell end.

2. The insertion instrument as set forth in claim 1 wherein said rod has a second end including biasing means for biasing said rod towards said first end of said shaft.

3. The insertion instrument as set forth in claim 1 wherein said shaft is a hollow tube and said rod is slidably mounted within said tube.

4. The insertion instrument as set forth in claim 3 wherein said rod has a second end including biasing means for biasing said rod towards said first end of said shaft.

5. The insertion instrument as set forth in claim 1 having a plurality of engagement elements for engaging a plurality of openings in the shell.

6. The insertion instrument as set forth in claim 1 wherein the cup open end extends along a plane.

7. A prosthesis implantation inserter for use with a part-spherical flexible acetabular cup which has an outer shell and a bearing element with an opening or openings in its peripheral rim extending from an equatorial region towards a polar region of the part-spherical cup, the opening or openings having curved edges comprising engagement means which in an operational position has chamfered edges sized to frictionally engage the curved edges of and circumferentially expand the opening or openings, and release means which can be operated to withdraw the engagement means from the openings or openings.

8. The prosthesis inserter as claimed in claim 7 in which the engagement means which contact the opening or openings is slightly larger then the openings.

9. The prosthesis implantation inserter as claimed in claim 7 which includes a locator adapted to locate the rim of the acetabular cup and in relation to which the engagement means can be moved by the release means.

10. The prosthesis implantation inserter as claimed in claim 9 in which the engagement means comprise a sliding component positioned in the locator.

11. The prosthesis implantation inserter as claimed in claim 7 in which the engagement means are resiliently biased towards the operational position.

12. A prosthesis implantation inserter as claimed in claim 7 in which the engagement means includes an engagement portion or portions which is or are shaped to cooperate with the shape of the opening or openings in the peripheral edge of the cup with which it is to be used.

13. The prosthesis implantation inserter as claimed in claim 12 in which the engagement portion is shaped to engage a keyhole-shaped opening in the peripheral edge of the cup with which it is adapted to be used.

14. The prosthesis implantation inserter as claimed in claim 12 in which the engagement portion is shaped to engage a substantially radially extending slot in the peripheral edge of the cup with which it is adapted to be used.

15. The prosthesis implantation inserter as claimed in claim 12 in which the engagement portions are shaped as a series of radially extending fins adapted to engage a series of radially extending openings in the form of slots in the peripheral edge of the cup with which it is to be used.

16. The prosthesis implantation inserter as claimed in claim 9 in which the locator is shaped to accommodate an acetabular cup with a rim which mimics the natural shape of the acetabulum.

17. The prosthesis implantation inserter as claimed in claim 7 including a body portion which carries the engagement means, a handle and a trigger which can operate the release means.

18. The prosthesis implantation inserter as claimed in claim 17 in which the body portion, handle and trigger are detachable from the engagement means.

19. The prosthesis implantation inserter as claimed in claim 18 in combination with a flexible acetabular cup with which it is to be used and in which the engagement means detach from the body portion, handle and trigger and engage in the cup are located in a sterile package.

20. The prosthesis implantation inserter as claimed in claim 7 in combination with an acetabular cup with which it is to be used.

* * * * *